United States Patent [19]

Sandbank

[11] Patent Number: 5,548,125
[45] Date of Patent: Aug. 20, 1996

[54] RADIATION PROTECTIVE GLOVE

[75] Inventor: Barry M. Sandbank, Saltney, United Kingdom

[73] Assignee: Smith & Nephew plc, London, England

[21] Appl. No.: 182,057

[22] PCT Filed: Jul. 16, 1992

[86] PCT No.: PCT/GB92/01302

§ 371 Date: Jan. 18, 1994

§ 102(e) Date: Jan. 18, 1994

[87] PCT Pub. No.: WO93/02457

PCT Pub. Date: Feb. 4, 1993

[30] Foreign Application Priority Data

Jul. 16, 1991 [GB] United Kingdom .................. 9115343
Oct. 31, 1991 [GB] United Kingdom .................. 9123121

[51] Int. Cl.⁶ ........................................................ G21F 3/02
[52] U.S. Cl. .................................... 250/519.1; 250/515.1; 250/516.1
[58] Field of Search ........................... 250/505.1, 515.1, 250/516.1, 519.1

[56] References Cited

U.S. PATENT DOCUMENTS

| | | |
|---|---|---|
| 3,075,925 | 1/1963 | Dunegin . |
| 3,608,555 | 9/1971 | Greyson ............................... 250/519.1 |
| 3,818,234 | 10/1972 | Atkins et al. ......................... 250/518.1 |
| 4,837,448 | 6/1989 | Banchelin et al. .................... 250/515.1 |
| 5,001,354 | 3/1991 | Gould et al. .......................... 250/516.1 |
| 5,245,195 | 9/1993 | Shah et al. ............................ 250/515.1 |
| 5,247,182 | 9/1993 | Servant et al. ........................ 250/516.1 |

FOREIGN PATENT DOCUMENTS 0242294  10/1987  European Pat. Off. .

*Primary Examiner*—Bruce C. Anderson
*Attorney, Agent, or Firm*—Larson and Taylor

[57] ABSTRACT

Radiation protection gloves for surgical and medical use which have a layer of flexible polymer containing at least 25% by volume of particulate tungsten material and a radiation absorbing capacity equivalent to that of 0.13 mm of lead. The glove preferably comprises an elastomer such as ethylene propylene diene copolymer.

14 Claims, 2 Drawing Sheets

RADIATION PROTECTIVE GLOVE

The present invention relates to radiation protective gloves and in particular radiation protective gloves for surgical or medical use and processes for their manufacture.

Surgeons and other medical personnel are often involved in medical procedures such as diagnostic, detection or guidance procedures in which their hands are exposed to radiation such as X-rays. In many of these procedures the field of operation is irradiated with X-rays so that the surgeon or other personnel can carry out the procedure using a fluoroscopic viewing screen. In diagnostic procedures using X-rays a radiologist may have to hold a patient such as an infant or in the case of veterinary work an animal to restrain the movement thereof. The dose of radiation received by a patient in any of these procedures will normally be well below the non-acceptable levels. Surgical or medical personnel who frequently carry out these procedures, however, may be exposed to radiation above the acceptable dose level. It is therefore desirable that these personnel wear protective gloves during the above procedures to limit or attenuate the amount of radiation received by the hands. Radiation protective gloves containing lead or lead oxide fillers are known in the art. Lead compounds, however, are toxic materials. Furthermore, gloves containing lead compounds can mark surfaces, for example, with a black mark. In addition it has been found that gloves with sufficient wall thickness or filler content to provide good radiation protection tend to be inflexible thereby making the gloves tiresome to wear and difficult to use by the wearer when handling instruments.

U.S. Pat. No. 5,001,354 discloses radiation protective gloves prepared by a latex dipping in a polymeric mixture comprising a dispersion of natural rubber latex and up to 20% by volume of tungsten filler which are capable of absorbing 50 to 80% incident radiation generated at voltages of 60 to 100 kVp. With gloves having the highest tungsten loading describe, the radiation absorbing capacity at higher radiation rates is limited.

The difficulty associated with the use of natural rubber latex-filler dispersion disclosed in the process of U.S. Pat. No. 5,001,354 is that even at the relatively lower filler contents disclosed therein has to be continuously agitated by a complex arrangement of pumps to maintain the tungsten filler in suspension, As a consequence it has been found almost impossible to prepare latex rubber dispersions with tungsten filler content higher than 20% by volume to provide gloves with a higher radiation protection than that given in the hereinabove US Patent because of the extremely fast settling rate of the high specific gravity tungsten filler.

It would be desirable to have gloves with an even higher radiation absorbing capacity to limit the effects of radiation exposure on the wearers' hands, It has now been found possible to achieve protection at higher radiation levels than with flexible gloves containing a higher tungsten filler content than 20% by volume. Such gloves can be made by relatively simple processes using a flexible polymer.

Accordingly the present invention provides a radiation protective glove for surgical or medical use comprising a layer of flexible polymer containing at least 25% by volume of particulate tungsten material and having a radiation absorbing capacity equivalent to that of at least 0.13 mm thickness of lead.

Gloves of the invention are preferably made of a flexible synthetic polymer. In another aspect, therefore, the present invention provides a radiation protective glove for surgical or medical use comprising a layer of flexible synthetic polymer containing at least 25% by volume of particulate tungsten material and having a radiation absorbing capacity equivalent to that of 0.13 mm thickness of lead.

The gloves of the invention will normally be used in situations where the wearer is exposed to X-rays generated at voltages up to 150 KVP.

The filled polymer layer of the gloves will have a radiation absorbing capacity equivalent of at least 0.13 mm thickness of lead, more suitably at least 0.25 mm thickness of lead and preferably a radiation absorbing capacity of at least 0.35 mm thickness of lead.

The lead thickness equivalent of a tungsten filled layer of a glove of the invention can be obtained by measuring the % transmission through a sample layer of an x-ray beam generate at 60 KVP and comparing it with the % transmission of a similar x-ray beam through a different thickness of lead foil.

% absorption or attenuation the radiation for a layer can be then obtained by subtracting the % transmission value from 100%.

FIG. 3 of the drawings shows a graph of % transmission versus lead thickness for x-ray beams generated at voltages of 60, 80, 100 and 120 KVP. FIG. 3 indicates that a layer with a lead thickness equivalent of at least 0.13 mm has a % absorption of about 90% for x-rays generated at 60 KVP and in excess of 80% for x-rays generated at 100 KVP.

Furthermore, it has been found that the tungsten filled polymer layers of gloves of the invention exhibit higher lead thickness equivalents with x-ray beams generated at higher voltages than that of 60 KVP.

Gloves of the invention are therefore capable of absorbing well in excess of 80% of the incident radiation at 60 to 100 KVP.

Gloves of the invention are capable of absorbing more suitably at least 85%, desirably at least 90% and preferably at least 95% of the incident radiation at 60 to 100 KVP.

Gloves of the invention therefore can provide greater protection to x-rays than the gloves disclosed in the hereinbefore mentioned prior art United States patent.

The amount of particulate tungsten material in the polymer layer of the gloves of the invention can be adapted to obtain a flexible layer with the desired radiation absorption capacity. Such an amount will be at least 25% by volume and can favourably be at least 30% by volume and can preferably be at least 40% by volume. Similarly the amount of particulate tungsten material in the polymer layer of the gloves of the invention can suitably be less than 90% by volume, more suitably less than 70% by volume and can preferably be less than 50% by volume.

Apt polymer layers for use in the invention contain 30% to 60% by volume and preferably 35% to 55% by volume of particulate tungsten material.

The tungsten material containing polymer layer of the gloves of the invention will not contain any holes which would allow the direct passage of x-rays. Surgical gloves of the invention will also be impermeable to aqueous liquids and bacteria to provide a barrier therefor.

The thickness of this layer can suitably be less than 1.5 mm, favourably be less than 1.00 mm and can preferably be less than 0.8 mm.

Similarly the thickness of the polymer layer can be suitably greater than 0.1 mm and can preferably be greater than 0.2 mm.

Apt polymer layers for use in the invention have a thickness of suitably 0.1–1.3 mm and preferably 0.2–1.0 mm.

The thickness of the tungsten material containing polymer layer can be adapted to provide a chosen radiation protection level (expressed as equivalent to a lead thickness) at a given filler volume percentage.

It is believed that gloves of the invention can advantageously provide a level of radiation protection equivalent to 0.5 mm of lead using glove polymer layer of less than 1 mm thick at particulate tungsten material loading of 40% by volume.

Apt gloves of the invention having a radiation protection level equivalent to 0.25 to 0.35 mm of lead can be provided using a 0.5–0.7 mm thick polymer layer containing 40% by volume of particulate tungsten material.

Tungsten material suitable for use in the gloves of the invention include tungsten metal and chemically inert compounds thereof such as tungsten oxide and tungsten carbide. However, a higher volume percentage of tungsten compound in the gloves is required to get the same radiation absorption protection as that of tungsten metal.

Tungsten materials advantageously have a higher specific gravity and a higher radiation absorption per unit thickness than that of lead material. As a consequence a layer containing tungsten material can provide higher relative radiation absorption and therefore higher radiation protection than that of similar layer containing the same volume percentage of lead material. Furthermore as herein before mentioned the tungsten filled polymer layer can provide higher than expected relative radiation absorption and protection from x-rays generated at voltages in excess of 60 KVP.

The tungsten material used in the invention will be in a particulate form such as a powder.

The tungsten material can have a particulate size of suitably less than 20 μm, favourably less than 10 μm and preferably less than 1 μm for example 0.5 to 0.9 μm.

The tungsten containing flexible polymer layer of the glove of the invention should be sufficiently flexible to enable the wearer to bend the finger portions of the glove without undue force, to hold instruments therewith and preferably also to obtain a sense of "touch" or "feel" through the walls of the glove.

Suitable flexible polymers for use in the invention can include any of the pharmaceutically acceptable and water insoluble synthetic polymers capable of forming flexible layers for use in gloves.

Such polymers include elastomeric polymers ie. elastomers and plasticised non-elastomeric polymers.

Favoured flexible polymers however are elastomeric polymers.

Suitable elastomers include those comprising natural rubber, butadiene homopolymers and its copolymers with styrene, isobutylene-isoprene copolymers, ethylene-propylene and ethylene-propylene-diene copolymers, polybutadiene acrylate, synthetic polyisoprene, polydimethylsiloxane and thermoplastic elastomers such as polyester-urethane, polyether-urethane, polyether-amide polyether-ester and A-B-A type block copolymers where A is styrene and B is butadiene, isoprene or ethylene butylene.

Aptly the flexibility of the polymer material employed in the gloves of the invention is at least 0.25 mm, more aptly at least 0.35 mm, and preferably at least 0.45 mm when determined by the following bend test method.

A list rig comprised two bars, 5 mm long, spaced 5 mm apart. The bars had an inverted V-shape to provide loading surfaces. A 13 mm×3 mm strip of polymer material was draped over the bars and a load of 100 mmN applied to the centre of the material for 2 minutes. The deflection of the material under the load was measured employing a Perkin-Elmer Thermo-Mechanical Analyzer. The deflection in millimeters is expressed as the flexibility.

Favoured elastomers include natural rubber, ethylene-propylene copolymers rubbers (EPM) and ethylene-propylene copolymers rubbers (EPDM) containing diene side chains derived from monomers such as 1, 4, hexadiene, dicyclopentadiene or ethylidenenorbornene monomers.

Flexible polymers such as elastomers for use in the invention can advantageously be cross-linked or cured to render the glove layer or layers tougher.

The presence of the pendant sites of unsaturation in EPDM rubbers enables these rubbers to be cross-linked or cured by conventional sulphur based rubber vulcanising systems.

A layer of flexible polymer such as an elastomer used in the invention can optionally contain a plasticiser to render the glove layer or layers more flexible.

The EPM and EPDM rubbers can be readily plasticised by hydrocarbon oils such as aliphatic hydrocarbon oils to advantageously provide layers with very good flexibility.

The EPM and EPDM rubber layer used in the invention can suitably contain up to 50% by weight of hydrocarbon oil.

Suitable plasticised non-elastomeric polymers include plasticised vinyl chloride polymers and copolymers.

A flexible polymer layer used in the invention can optionally contain optionally up to 25% by weight of a filler for example to reinforce the glove layer.

The tungsten containing polymer layer of a glove of the invention can be provided with a protective coating of a flexible polymer such as an elastomer on its inner or outer surface and on both such surfaces. Such a coating can suitably be less than 100 μm thick and can preferably be less than 75 μm thick. Apt coatings are 10 to 50 μm thick. Such protective coatings are preferably on the finger or palm portions of the glove.

The tungsten containing polymer layer may comprise a flexible reinforcing layer to improve the tear and puncture resistance of the polymer layer. Suitable reinforcing layers include films of a polymer such as polyurethane, polyethylene, ethylene-vinyl-acetate copolymer, non-woven fabrics or plastics nets.

The reinforcing layer may be laminated to the surface of the filled polymer layer or included within the layer.

In a further aspect the present invention provides a process of forming a radiation protective glove having a radiation absorbing capacity equivalent to that of at least 0.13 mm thickness of lead which comprises forming the glove from a polymeric composition comprising a flexible polymer and containing at least 25% by volume of particulative tungsten material.

The gloves of the invention may be formed by any convenient moulding or fabrication process.

The gloves may be produced by a process which comprises forming one or more flexible sheets of synthetic polymer containing at least 25% by volume of particulate tungsten material, cutting one or more shaped glove pieces from the sheet or sheets and joining he glove shaped glove piece or pieces at the peripheral edges or margins thereof to form a glove.

Suitable shaped glove pieces include a foldable piece having the outline of two opposed glove halves joined for example at the base wrist portions thereof, two glove shaped opposed halves, and individual portions of these shaped pieces.

The cutting of the sheet or sheets can conveniently be carried out by a stamping method using shaped dies.

The sheet or sheets of tungsten filled polymer can be formed by mixing the appropriate amounts of polymer, tungsten powder and optionally plasticiser and/or filler into the polymer in a conventional rubber mixer such as a heated rubber planetary or Banbury mixer or on a rubber two roll mill and then extruding, casting or calendering the polymer mixture at a suitable temperature onto a cooled smooth surface or substrate.

A sheet containing a cross-linking agent of the polymer may be post cured by a suitable heating means.

The sheet so formed can conveniently be a continuous sheet from which the shaped glove pieces can be cut.

The glove pieces can be joined by a conventional heat-sealing or adhesive process.

The glove may be produced by a process which comprises moulding a flexible polymer containing at least 25% by volume of particulate tungsten material.

The polymer, filler and optionally plasticiser mixture can be formed by the processes hereinbefore described.

Suitable moulding processes include processes in which a glove former is sprayed with or dipped into a solution hot melt or powder suspension of the polymer mixture, processes which comprises injection-moulding compression moulding or thermo-forming a melt or plastic mass of the polymer mixture and processes which comprise forming, for example, vacuum forming a sheet of the polymer mixture in a heated mould.

Such moulding processes may advantageously provide seamless gloves.

The glove may be cured during moulding for example during a reaction injection moulding or after moulding.

Gloves of the invention are suitable for surgical or medical use. The gloves can be made to provide a radiation absorption equivalent to that of standard thickness of lead typically 0.13 mm, 0.25 mm, 0.35 mm or 0.5 mm thickness of lead. The thinner wall gloves, which meet one of the two lower standards of lead equivalent radiation protection, will normally be suitable for surgical use. The thicker wall gloves, which meet one of the two higher standards of lead equivalent radiation protection will normally be suitable for medical diagnostic use. Such thicker wall gloves which may e in the form of a gauntlet may also be suitable for non-medical uses for example in the nuclear field.

All these gloves of the invention, however, will advantageously provide greater radiation protection than that the gloves disclosed in U.S. Pat. No. 5,001,354.

The invention will now be illustrated by reference to the drawings and the examples which follow.

EXAMPLE 1

Figure 1:
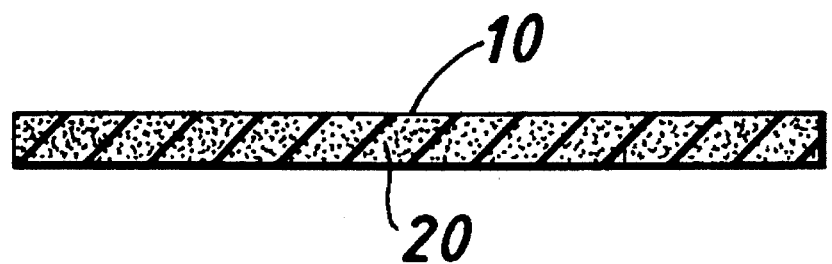
FIG.1 is a diagrammatic cross-sectional view which shows flexible layer (10) in accordance with the invention where the layer comprises a flexible polymer containing at least 25% by volume of particulate tungsten material (20)
Figure 2:
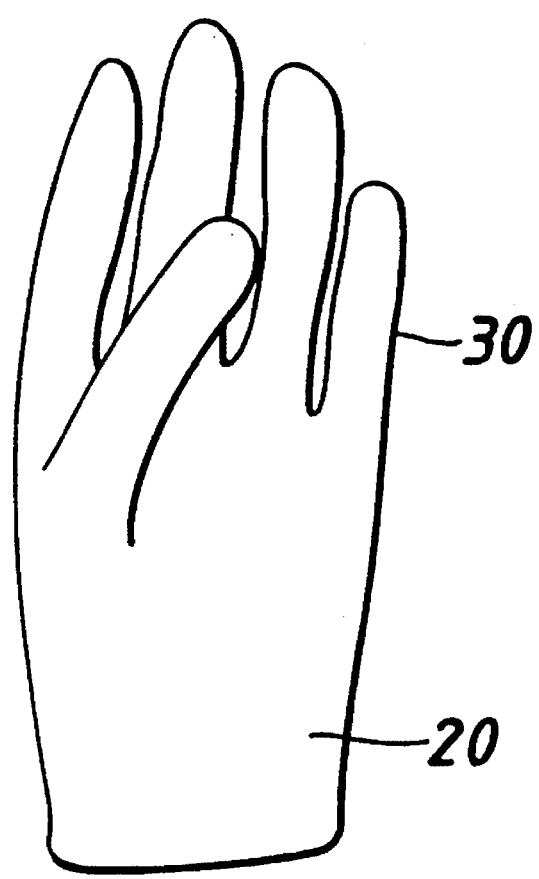
FIG. 2 is a diagrammatic view of a glove (30) of the invention where the glove (30) comprises a layer of flexible polymer containing at least 25% by volume of particulate tungsten material (20)
Figure 3:
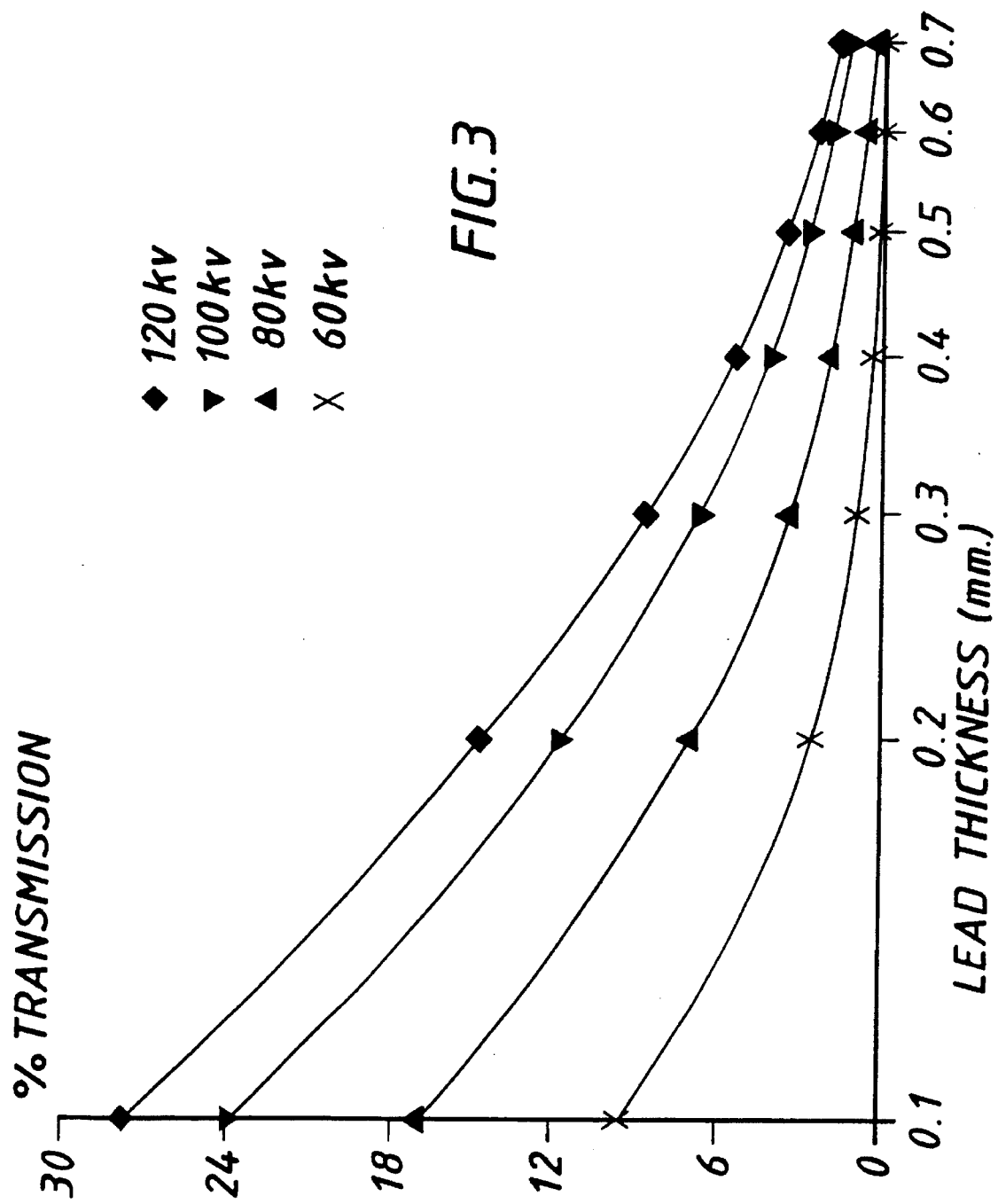
FIG. 3 shows a graph illustrating the percentage transmission of x-rays, through a range of lead thicknesses generated at a number of voltages.

A 0.33 mm thick flexible sheet of ethylene-propylene-diene (EPDM) rubber containing 40% by volume of particulate tungsten metal (marketed by James Walker Co) was cut to form a pair of opposed glove shape pieces. The pieces of sheet were adhered at their peripheral margins or edges to form a seamed glove of the invention.

The glove wall was sufficiently flexible to allow a volunteer wearer to bend the finger portions of the glove and to pick up and hold medical instruments without the exertion of undue force.

The glove had radiation absorption capacity equivalent to 0.13 mm thickness of lead. The glove was therefore highly suitable for protecting the wearer from x-rays generated at 121 KVP and lesser voltages.

EXAMPLE 2

A natural rubber composition containing 38% by volume of tungsten was compression moulded using heated glove shaded made and female moulds to form a glove having an average wall thickness of about 0.71 min.

The glove wall was sufficiently flexible to allow a volunteer wearer to bend the finger portions of the glove and to pick up and hold medical instruments without the exertion of undue forces.

The glove had radiation absorption capacity equivalent to 0.35 mm of lead. This absorption capacity was confirmed by x-ray photography by comparing the x-ray shielding provided by a sample of the glove with a 0.35 mm sheet of lead.

The glove was therefore highly suitable for protecting the wearer from x-rays generated at 121 KVP and lesser voltages.

EXAMPLES 3

A glove of the invention were made in same manner as Example 1 using a 0.55 mm thick flexible sheet of cross-linked ethylene-propylene-diene (EPDM) rubber containing 40% by volume of particulate tungsten metal. The sheet layer also contained a paraffin based plasticiser (44% by weight of rubber) and silica reinforcing filler (15% by weight of rubber).

The glove was sufficiently flexible to allow a volunteer wearer to pick up and hold medical instruments without undue force and had flexibility (as hereinbefore defined) of 0.476 mm.

The glove had a radiation absorption capacity equivalent to 0.25 mm (at 60 KVP) thickness of lead.

The % absorption values of sample layers was measured using x-rays generated at 60, 80 100 and 120 KVP and compared with % absorption values obtained 0.25 mm of lead using x-rays generated in the same range of beam values.

The results were as follows:

| Beam Voltage (kvp) | Absorption(%) 0.25 mm lead | Layer of Ex 3 |
| --- | --- | --- |
| 60 | 98.5% | 98.5% |
| 80 | 95.2% | 96.5% |
| 100 | 91.3% | 95.0% |
| 120 | 88.8% | 93.6% |

The results show that the glove of Example 3 had a radiation absorbency capacity well in excess of 80%. Furthermore the results indicate that gloves of the invention have a higher radiation absorbing capacity to x-ray beams generated at voltages above 60 KVP and hence higher equivalent lead thickness than 0.25 mm thickness of lead.

I claim:

1. A radiation protective glove for surgical and medical use comprising a layer of flexible polymer containing at least 25–90% by volume of particulate tungsten material and having a radiation absorbing capacity equivalent to that of at least 0.13 mm thickness of lead said layer of the glove being of a thickness of 0.1 to 1.3 mm and being sufficiently flexible to enable the wearer to bend finger portions of the glove without undue force, to hold instruments, and to obtain a sense of touch and feel through the walls of the glove.

2. A radiation protective glove according to claim 1 having radiation absorbing capacity equivalent to that of 0.13 mm thickness of lead.

3. A glove as claimed in claim 1 in which the polymer is an elastomeric polymer.

4. A glove as claimed in claims 3 in which the elastomeric polymer comprises an ethylene propylene or ethylene propylene diene copolymer.

5. A glove as claimed in claim 4 in which the elastomeric polymer contains up to 50% by weight of hydrocarbon plasticiser.

6. A glove as claimed in claim 1 which has a radiation capacity equivalent to that of at least 0.25 mm thickness of lead.

7. A glove as claimed in claim 1 which has a radiation capacity equivalent to that of at least 0.35 mm thickness of lead.

8. A glove as claimed in claim 1 in which the polymer layer has a thickness of 0.2 mm to 1.0 mm.

9. A glove as claimed in claim 1 which in the polymer layer contains 30% to 60% by volume of particulate tungsten material.

10. A glove as claimed in claim 1 which is capable of absorbing at least 85% of the incident radiation generated at voltages of 60 to 100 kVp.

11. A glove as claimed in claim 1 which is capable of absorbing at least 90% of the incident radiation generated at voltages of 60 to 100 kVp.

12. A glove as claimed in claim 1 which is capable of absorbing at least 95% of the incident radiation generated at voltages of 60 to 100 kVp.

13. A process for forming a flexible radiation protective glove for surgical and medical use having a radiation absorbing capacity equivalent to that of at least 0.13 mm thickness of lead which comprises forming the glove from a polymer composition comprising a flexible polymer and containing at least 25–90% by volume of a particulate tungsten material, said glove being sufficiently flexible to enable the wearer to bend finger portions of the glove without undue force, to hold instruments, and to obtain a sense of touch and feel through the walls of the glove, and wherein said wall of the glove has a thickness of 0.1 to 1.3 mm.

14. A process as claimed in claim 11 in which the forming step comprises a moulding step.

* * * * *